United States Patent [19]
Shimizu et al.

[11] Patent Number: 5,866,708
[45] Date of Patent: Feb. 2, 1999

[54] PROCESS FOR PRODUCING α β-UNSATURATED NITRILE

[75] Inventors: Hideyuki Shimizu, Yokosuka; Masanobu Ohta, Gunma, both of Japan

[73] Assignee: Asahi Kasei Kogyo Kabushiki Kaisha, Osaka, Japan

[21] Appl. No.: 930,857

[22] PCT Filed: Apr. 5, 1996

[86] PCT No.: PCT/JP96/00945

§ 371 Date: Oct. 7, 1997

§ 102(e) Date: Oct. 7, 1997

[87] PCT Pub. No.: WO96/31465

PCT Pub. Date: Oct. 10, 1996

[30] Foreign Application Priority Data

Apr. 7, 1995 [JP] Japan .................................. 7-082877

[51] Int. Cl.$^6$ ................................................. C07C 253/00
[52] U.S. Cl. ............................................................. 558/320
[58] Field of Search .............................................. 558/320

[56] References Cited

U.S. PATENT DOCUMENTS

| | | |
|---|---|---|
| 4,801,731 | 1/1989 | Jordan . |
| 4,849,537 | 7/1989 | Ramachandran et al. .............. 558/320 |
| 4,849,538 | 7/1989 | Ramachandran et al. .............. 558/320 |
| 5,256,810 | 10/1993 | Rowe et al. . |

FOREIGN PATENT DOCUMENTS

| | | |
|---|---|---|
| 0446379 | 9/1991 | European Pat. Off. . |
| 1265770 | 3/1972 | United Kingdom . |

*Primary Examiner*—Johann Richter
*Assistant Examiner*—Joseph Murray
*Attorney, Agent, or Firm*—Birch, Stewart, Kolasch & Birch, LLP

[57] ABSTRACT

A process for producing an α,β-unsaturated nitrile, the process comprising the step of: reacting (1) a hydrocarbon selected from an olefin selected from propylene and isobutylene, a paraffin selected from propane and butane, and tertiary butyl alcohol, (2) ammonia, and (3) an oxygen-containing gas, in a reactor at a high temperature in a gas phase over a fluidized bed, so as to prepare an α,β-unsaturated nitrile having the same number of carbon atoms as the hydrocarbon as a starting material, the reactor comprising a reactor vessel having therein, from a bottom of the reactor vessel, an oxygen-containing gas dispersing plate or pipe and a mixed gas dispersing pipe for dispersing a mixed gas of the hydrocarbon and the ammonia, a pressure loss in the oxygen-containing gas dispersing plate or pipe is controlled to the range of from 0.6 to 3.0 times a pressure loss in the fluidized bed.

14 Claims, 2 Drawing Sheets

5,866,708

PROCESS FOR PRODUCING α β-UNSATURATED NITRILE

This application is a 371 of PCT/JP96/00945 filed Apr. 5, 1996.

TECHNICAL FIELD

The present invention relates to a process for producing an α,β-unsaturated nitrile which comprises the ammoxydation of propylene, isobutylene, tertiary butyl alcohol, propane or butane to prepare an α,β-unsaturated nitrile having the same number of carbon atoms as the olefin, paraffin or tertiary alcohol used as a starting material in a high yield.

More particularly, the present invention relates to a process for producing an α,β-unsaturated nitrile using a novel reactor for effecting the gas phase reaction of ammonia, an oxygen-containing gas and an olefin, tertiary butyl alcohol or paraffin over a fluidized bed to produce an unsaturated nitrile such as acrylonitrile and methacrylonitrile, wherein the reactor is arranged such that the pressure loss in an orifice attached to the jetting portions in an oxygen-containing gas dispersing plate or pipe and the pressure loss in an orifice attached to jetting portions in a pipe for dispersing a mixture of ammonia, and an olefin, tertiary butyl alcohol or paraffin (hereinafter referred to as "mixed gas") are controlled.

BACKGROUND ART

Ammoxydation has long been industrially practiced. Many improvements have been made for ammoxydation from the standpoint of catalyst. However, few proposals have been made for the structure of an apparatus (sparger) for supplying and spraying the starting material. It is disclosed in U.S. Pat. No. 4,801,731 (JP-A-2-258 (The term "JP-A" as used herein means an "unexamined published Japanese patent application")). All these proposals feature the disposition of an oxygen gas exit orifice and a propylene/ammonia exit orifice opposed to each other.

British Patent 1,265,770 describes the provision of a sparger disposed in the form of a ring on the peripheral portion of the reactor. However, the object of this arrangement is to prevent the accumulation of a catalyst on the peripheral portion of the reactor. No reference is made to reactivity.

Few proposals have been made for the structure of dispersing plate or dispersing pipe. In particular, the pressure loss in a dispersing plate or dispersing pipe is disclosed in Daizo Kunii, *Fluidization Engineering*, Octave Levenspiel, John Wiley & Sons. Inc., page 87 (1969). In this reference, 0.1 times the pressure loss in a fluidized bed is recommended as the pressure loss required for fluidized gas dispersing pipe or dispersing plate. However, it was found that if gases are supplied through two systems in an industrial scale apparatus having a column diameter of not less than 3 m, the distribution of the supplied gas concentration is localized under the foregoing conditions, resulting in the reduction of the yield of the objective unsaturated nitrile.

DISCLOSURE OF THE INVENTION

An object of the present invention is to provide a process for producing an α,β-unsaturated nitrile by an ammoxydation reaction, particularly by the supply of reaction gases through two system, in which the conversion of the reaction is enhanced by focusing the local distribution of concentration of reaction gases in the reactor.

The above and other objects and effects of the present invention will be more apparent from the following description.

The present invention relates to a process for producing an α,β-unsaturated nitrile, the process comprising the step of:

reacting a hydrocarbon selected from an olefin selected from propylene and isobutylene, a paraffin selected from propane and butane, and tertiary butyl alcohol; ammonia; and an oxygen-containing gas, in a reactor at a high temperature in a gas phase over a fluidized bed, so as to prepare an α,β-unsaturated nitrile having the same number of carbon atoms as the hydrocarbon as a starting material, the reactor comprising a reactor vessel having therein, from a bottom of said reactor vessel, an oxygen-containing gas dispersing plate or pipe and a mixed gas dispersing pipe for dispersing a mixed gas of the hydrocarbon and said ammonia, a pressure loss in the oxygen-containing gas dispersing plate or pipe is controlled to the range of from 0.6 to 3.0 times a pressure loss in the fluidized bed.

BEST MODE FOR PRACTICING THE INVENTION

Figure 1:
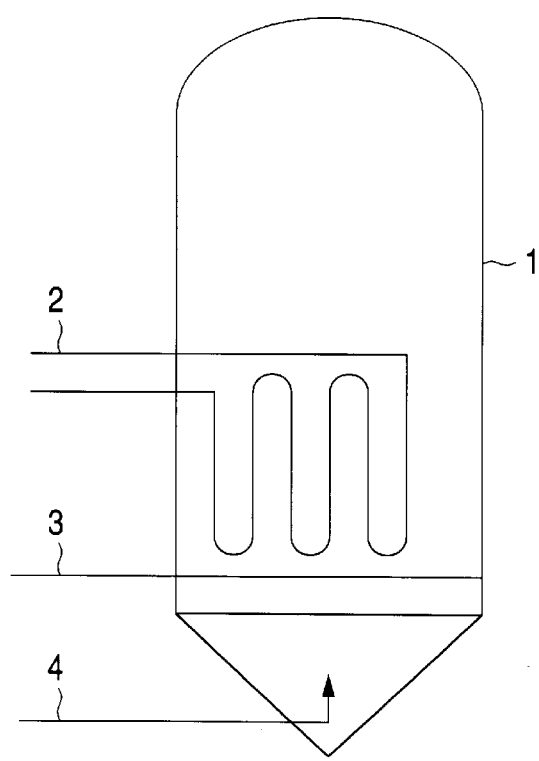
FIG. 1 shows a vertical sectional view of one embodiment of a fluidized bed reactor used in the present invention.

The present inventors have made extensive studies of apparatus and conditions for production of unsaturated nitrile over a fluidized bed. As a result, a surprising fact has been found that the static pressure difference between the peripheral portion of the reactor and the central portion of the reactor in a large scale industrial apparatus having a column diameter of not less than 3 m can reach not less than 200 mm/H$_2$O in some cases. Furthermore, among various conditions and structural factors such as dispersing pipe, such a static pressure difference has been found to influence the yield of the unsaturated nitrile. It has been thus found that by eliminating the effect of static pressure difference, the yield of the unsaturated nitrile can be improved.

Ammoxydation reaction applied to the present invention has long been known. In this reaction; a hydrocarbon selected from an olefin selected from propylene and isobutylene, a paraffin selected from propane and butane, and tertiary butyl alcohol; ammonia; and an oxygen-containing gas are reacted at a high temperature in a gas phase in the presence of a catalyst in a fluidized bed reactor to produce a corresponding α,β-unsaturated nitrile.

The present invention relates to a process for producing an α,β-unsaturated nitrile, comprising reacting a hydrocarbon selected from an olefin selected from propylene and isobutylene, a paraffin selected from propane and butane, and tertiary butyl alcohol; ammonia; and an oxygen-containing gas, in a reactor at a high temperature in a gas phase over a fluidized bed, so as to prepare an α,β-unsaturated nitrile having the same number of carbon atoms as the hydrocarbon as a starting material.

The reactor used in the present invention comprises a reactor vessel having therein, from a bottom of the reactor vessel, an oxygen-containing gas dispersing plate or pipe and a mixed gas dispersing pipe for dispersing a mixed gas of said hydrocarbon and said ammonia, and the pressure loss in the oxygen-containing gas dispersing plate or pipe is controlled to the range of from 0.6 to 3.0 times, preferably from 1.0 to 3.0 times, the pressure loss in the fluidized bed.

The pressure loss in the mixed gas dispersing pipe is preferably controlled to the range of from 0.6 to 5.0 times, more preferably from 1.0 to 5.0 times, the pressure loss in said fluidized bed.

It is more preferred that the pressure loss in the mixed gas dispersing pipe is greater than that of the oxygen-containing gas dispersing plate or pipe.

In a preferred embodiment of the present invention, the pressure loss in the oxygen-containing gas dispersing pipe or plate and that of the mixed gas dispersing pipe can be controlled to desired values by adjusting the opening area of the orifice (orifice area)×(number of orifices).

Since the composition of gases to be supplied into the fluidized bed reactor is a high temperature olefin, paraffin or tertiary alcohol falling within its explosion limit, the mixture of the olefin, paraffin or tertiary alcohol and ammonia (hereinafter referred to as "mixed gas") needs to be supplied separately from the oxygen-containing gas.

An embodiment of the present invention will be described with reference to FIGS. 1, 2 and 3, but the present invention is not construed as being limited thereto.

FIG. 1 is a vertical sectional view of a fluidized bed reactor. Numeral 1 denotes a main body of the fluidized bed reactor (reactor vessel); 2 denotes a heat-removing coil; 3 denotes a "mixed olefin gas" dispersing pipe; and 4 denotes an oxygen-containing gas introducing pipe.

Figure 2:
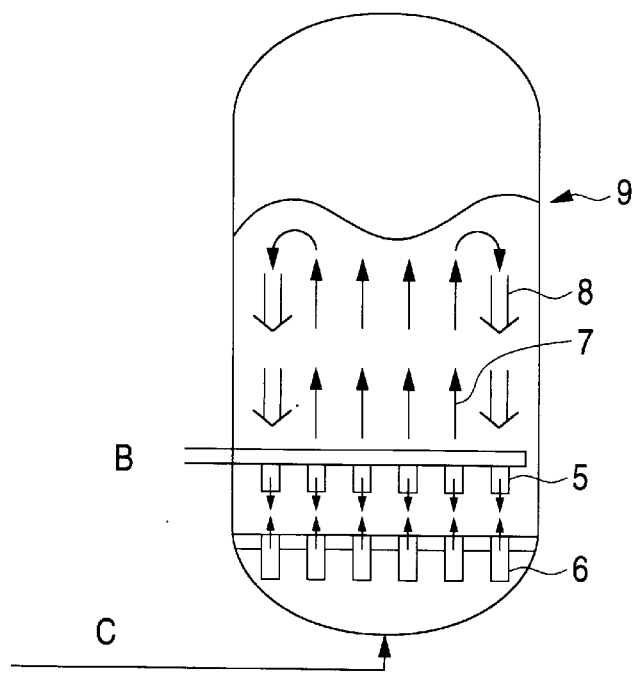
FIG. 2 illustrates a schematic view of an example of the fluidized bed reaction used in the present invention.
Figure 3:
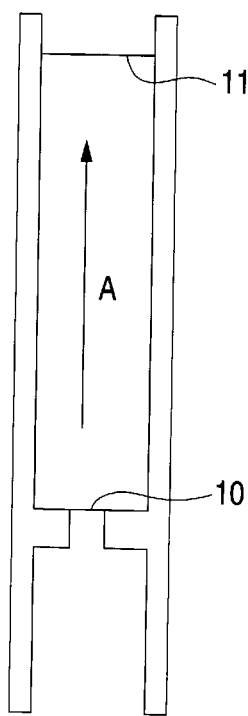
FIGS. 3(a), 3(b), 3(c), and 3(d) each shows an example of a vertical sectional view of a nozzle used in the present invention.
Figure 3:
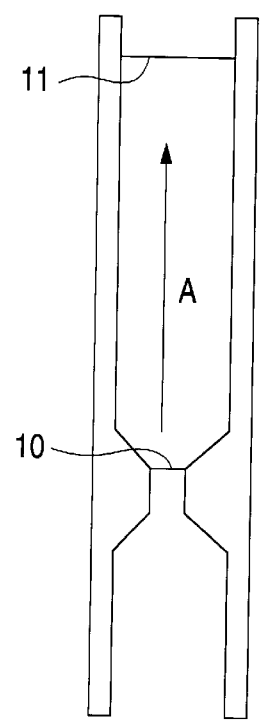
Figure 3:
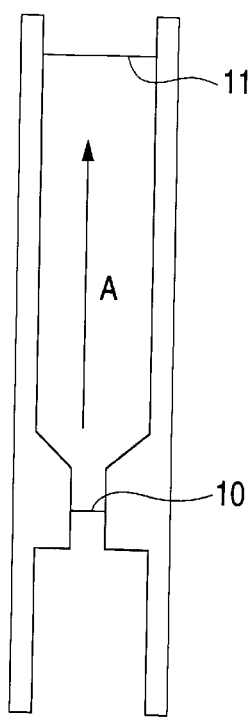
Figure 3:
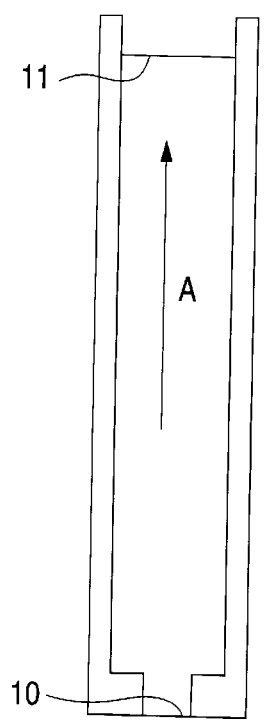

FIG. 2 illustrates an example of the positioning of various nozzles featuring the present invention and a schematic view of circulation of catalyst particles. Numerals 5 denotes a nozzle in "mixed olefin gas" dispersing pipe which is generally disposed at the bottom of the reactor; 6 denotes a nozzle for the oxygen-containing gas; 7 denotes upward flow in the circulating flow of the fluidized bed catalyst particles; 8 denotes downward flow in the circulation of the catalyst particles; and 9 denotes the interface of the catalyst bed. Symbol B denotes the mixed gas and C denotes the oxygen-containing gas. It is known that the catalyst density shows a sudden drop at a position above this interface. In the present invention, a "mixed olefin gas" dispersing pipe is disposed above the oxygen-containing gas dispersing plate or dispersing pipe.

FIGS. 3(a), 3(b), 3(c), and 3(d) illustrate embodiments of the nozzle for supplying a gas to be used in the present invention. Numeral 10 denotes an orifice portion for adjusting the differential pressure, and 11 denotes a shroud portion for jetting the gas. Symbol A denotes a gas jetting direction.

In the present invention, when the static pressure difference between the peripheral portion of the reactor and the central portion of the reactor was measured by using upwardly open pressure taps, the peripheral portion of the reactor showed 200 mm/$H_2O$ higher than the central portion of the reactor in some cases. When the static pressure difference between the peripheral portion of the reactor and the central portion of the reactor was measured using a pressure tap which is downwardly open as similar to the mixed gas dispersing pipe nozzle, the central portion of the reactor showed a higher value than the peripheral portion of the reactor, the difference therebetween being greater than that obtained with upwardly open pressure taps. When the static pressure difference between the peripheral portion of the reactor and the central portion of the reactor is great, the difference in the concentration of unreacted olefin between the peripheral portion of the reactor and the central portion of the reactor is great, reducing the yield.

Thus, in the present invention, the pressure loss in the oxygen-containing gas dispersing plate or pipe and, in a preferred embodiment, the mixed gas dispersing pipe are each adjusted to not less than 0.6 times, preferably not less than equal to that in the fluidized bed. Since the static pressure difference can be absolutely or relatively reduced by controlling these pressure losses to the above range, the conversion at the peripheral portion of the reactor is remarkably enhanced as compared with the case where the static pressure difference deviates from this range, resulting in the enhancement of the conversion in the reactor. The upper limit of the pressure loss in the oxygen-containing gas dispersing plate or pipe can be determined mainly by the economical efficiency of a gas compressor and is generally not more than 3 times the pressure loss in the fluidized bed. The upper limit of the pressure loss in the mixed gas dispersing pipe can be determined by the operating pressure of a chiller for olefin and ammonia from the standpoint of process and is generally not more than 5 times the pressure loss in the fluidized bed.

In the present invention, it is preferred that the opening area (orifice area)×(number of orifices) of the oxygen-containing gas dispersing plate or pipe and that of the mixed gas dispersing pipe are properly adjusted to keep the pressure loss in these dispersing plates or pipes to the foregoing ranges. For example, the opening ratio of the orifice (opening area of orifice)/(sectional area of reactor) of the oxygen-containing gas dispersing plate or pipe is preferably controlled to the range of from 0.10 to 1.0%, more preferably 0.12 to 0.35%, to realize the desired pressure loss defined herein. The orifice opening ratio of the orifice (opening area of orifice)/(sectional area of reactor) of the mixed gas dispersing pipe is preferably controlled to the range of from 0.01 to 0.2%, more preferably from 0.015 to 0.15%.

The pressure loss in the dispersing plates or pipes is generally proportional to the square of the gas flow rate and inversely proportional to the open area (orifice area)×(number of orifices). It also depends on the supplied amount of gas or the reactor pressure. Therefore, the pressure loss may be properly controlled by changing the temperature or pressure conditions.

Even if the orifice opening ratio is constant, the pressure loss varies with the area of the shroud portion (gas jetting portion).

The more the (orifice area)/(shroud area) ratio is, the less is the pressure loss.

In the present invention, it is preferred that the ratio of a sectional opening area of the orifice portion to that of the shroud portion (sectional opening area of orifice portion/sectional opening area of shroud portion) of the oxygen-containing gas dispersing plate or pipe and that of the mixed gas dispersing pipe is from 0.05 to 0.50, more preferably from 0.10 to 0.40.

In the present invention, the pressure loss in the fluidized bed is the ratio of (the weight of catalyst)/(the sectional area of the reactor), which can be determined by the difference between the pressure developed at the interface 9 of the catalyst bed in the reactor having a fluidized catalyst and the pressure developed directly above (0.1 m) the oxygen-containing gas dispersing plate or pipe. The weight of the catalyst bed required for the fluidized bed reactor can be properly determined by the activity of the catalyst, the feed rate of the reaction materials and the desired conversion.

In general, the amount of the catalyst is determined such that the time during which the catalyst comes into contact with the reactive gas is kept to about 1 to 20 seconds, preferably 2 to 12 seconds.

The pressure loss in the oxygen-containing gas dispersing plate or dispersing pipe is the difference between the pressure developed below the oxygen-containing gas dispersing plate or inside the oxygen-containing gas dispersing pipe and the pressure developed above the oxygen-containing gas dispersing plate or outside the oxygen-containing gas dispersing pipe. It is measured by means of a pressure tap disposed below the oxygen-containing gas dispersing plate or inside the oxygen-containing gas dispersing pipe and above (0.05 m) the oxygen-containing gas dispersing plate or dispersing pipe.

The pressure loss in the mixed gas dispersing pipe is the difference between the pressure developed inside the mixed gas dispersing pipe and the pressure developed outside the mixed gas dispersing pipe. It is measured by means of a pressure tap disposed inside the mixed gas dispersing pipe and that disposed outside the mixed gas dispersing pipe.

Taking into account the fact that the required pressure loss in the oxygen-containing gas dispersing plate has been given as a requirement for the absence of fixed bed in the reactor and the pressure loss in the mixed gas dispersing pipe has not been considered important as the required pressure loss in the oxygen-containing gas dispersing plate, it is a very surprising fact that the fulfillment of these requirements can provide remarkable enhancement of the conversion at the peripheral portion of the reactor and hence in the entire reactor in the present invention.

While the diameter and constitution of the reactor used in the present invention is not particularly limited, the diameter of the reactor vessel is preferably 3 m or more since in such an industrial scale apparatus, the localized distribution of the supplied gas tends to be remarkable.

As the catalyst employable in the present invention, any catalyst known as ammoxydation or oxidation catalyst, e.g., molybdenum-bismuth-iron-supported catalyst, can be used.

The reaction may be effected under known conditions described in known references and patents. By way of example, ammoxydation reaction for the production of α,β-unsaturated nitrile may be effected under the following conditions.

The amount of the oxygen-containing gas (such as air) to be supplied into the reactor as a starting material is generally from 5 to 15 mols, preferably from 7 to 14 mols, per mol of the olefin, paraffin or tertiary alcohol. The oxygen-containing gas is supplied into the reactor at the bottom thereof in such a manner that the temperature thereof is generally from 50° to 500° C., preferably from 100° to 400° C., directly after supplied. The amount of ammonia to be supplied is generally from 0.6 to 2 mols, preferably from 1 to 1.5 mols, per mol of the olefin, paraffin or tertiary alcohol.

The reaction temperature is generally from 350° C. to 600° C., preferably from 400° C. to 500° C. The reaction pressure is generally not more than 3 kg/cm²-G, preferably from 0.2 to 1.5 kg/cm²-G.

The olefin selected from propylene and isobutylene is preferably used as the hydrocarbon as the starting material.

EXAMPLE

The process of the present invention will be further described in the following examples and comparative examples.

The pressure loss in the fluidized bed as used in the following examples and comparative examples is the difference between the pressure developed at the top of the reactor and the pressure developed at a pressure tap disposed 100 mm above the dispersing plate.

The pressure loss in the oxygen-containing gas dispersing plate is the difference between the pressure developed below the oxygen-containing gas dispersing plate and the pressure developed at the foregoing pressure tap. The pressure loss in the mixed gas dispersing pipe is the difference between the pressure developed inside the mixed gas dispersing pipe and the pressure developed at the foregoing pressure tap.

As a measure of the conversion, the concentration of unreacted olefin at the central portion and peripheral portion of the reactor was used. For the measurement of the concentration of unreacted olefin, a gas sampling nozzle was disposed at a position in the central portion satisfying the relationship r/R=0.0 (wherein r is the distance from the center of the reactor, and R is the reactor radius) at a height of 9 m and at a position in the peripheral portion satisfying the relationship r/R=0.9 at the same height. The gas discharged from these sampling nozzles were washed with water, and then analyzed by gas chromatography. As the instruments and other attachments there may be used commonly used facilities having ordinary tolerance.

Example 1

The reactor used had a diameter of 7.8 m. The catalyst used was a molybdenum-bismuth-iron-supported catalyst having a particle diameter of from 10 to 100 μm and an average particle diameter of 50 μm. The reactor was filled with the catalyst in such an arrangement that the height of the static bed reached 2 m. As an air dispersing plate there was used a dispersing plate having an aperture diameter of 16.5 mm, a ratio (sectional opening area of orifice portion) /(sectional opening area of shroud portion) of 0.35, and 560 orifices. For the mixture of propylene and ammonia, a sparger having 560 nozzles attached to orifices with an aperture diameter of 6.2 mm was used. Air was supplied into the reactor at the bottom of the fluidized bed at a rate of 41,000 Nm³/H and a temperature of 250° C., and propylene and ammonia were supplied at a rate of 4,000 Nm³/H and 4,800 Nm³/H, respectively, and a temperature of 150° C. The reaction was effected at a temperature of 450° C. under a pressure of 1 kg/cm²-G. During this procedure, the pressure loss in the air dispersing plate was 1,300 mm/H₂O. The pressure loss in the propylene/ammonia sparger was 2,100 mm/H₂O. The pressure loss in the fluidized bed was 2,100 mm/H₂O. The results set forth in Table 1 were obtained.

TABLE 1

|  | Unreacted propylene (vol %) |
| --- | --- |
| Central portion | 0.12 |
| Peripheral portion | 0.22 |

Example 2

The reaction was effected in the same reactor as used in Example 1 under the same conditions as used in Example 1 except that a dispersing plate having 560 orifices with an aperture diameter of 14.0 mm was used as the air dispersing plate, a sparger having 560 nozzles attached to orifices with an aperture diameter of 4.7 mm was used for the mixture of propylene and ammonia, and the temperature of air to be supplied was 380° C. During this procedure, the pressure loss in the air dispersing plate was 2,100 mm/H$_2$O. The pressure loss in the propylene/ammonia sparger was 4,400 mm/H$_2$O. The pressure loss in the fluidized bed was 2,100 mm/H$_2$O. The results set forth in Table 2 were obtained.

TABLE 2

|  | Unreacted propylene (vol %) |
| --- | --- |
| Central portion | 0.11 |
| Peripheral portion | 0.18 |

Example 3

The reaction was effected in the same reactor as used in Example 1 under the same conditions as used in Example 1 except that a sparger having the same orifice aperture diameter as used in Example 1 but having an air jetting portion (shroud portion) aperture diameter 0.8 times greater than Example 1 (the ratio (sectional opening area of orifice portion)/(sectional opening area of shroud portion):0.55) was used as the sparger as air dispersing plate. During this procedure, the pressure loss in the air dispersing plate was 1,100 mm/H$_2$O. The pressure loss in the mixed gas dispersing pipe was 2,100 mm/H$_2$O. The pressure loss in the fluidized bed was 2,100 mm/H$_2$O. The results set forth in Table 3 were obtained.

TABLE 3

|  | Unreacted propylene (vol %) |
| --- | --- |
| Central portion | 0.11 |
| Peripheral portion | 0.28 |

Example 4

The reaction was effected in the same reactor as used in Example 1 under the same conditions as used in Example 1 except that a dispersing plate having 560 orifices with an aperture diameter of 14.0 mm was used as the air dispersing plate and a sparger having 560 nozzles attached to orifices with an aperture diameter of 4.7 mm was used for the mixture of propylene and ammonia. During this procedure, the pressure loss in the air dispersing plate was 2,400 mm/H$_2$O. The pressure loss in the propylene/ammonia sparger was 4,400 mm/H$_2$O. The pressure loss in the fluidized bed was 2,100 mm/H$_2$O. The results set forth in Table 4 was obtained.

TABLE 4

|  | Unreacted propylene (vol %) |
| --- | --- |
| Central portion | 0.06 |
| Peripheral portion | 0.10 |

Comparative Example 1

The reaction was effected in the same reactor as used in Example 1 under the same conditions as used in Example 1 except that a dispersing plate having 560 nozzles attached to orifices with an aperture diameter of 20 mm was used as the air dispersing plate and a sparger having 560 nozzles attached to orifices with an aperture diameter of 13 mm was used for the mixture of propylene and ammonia. During this procedure, the pressure loss in the air dispersing plate was 600 mm/H$_2$O. The pressure loss in the propylene/ammonia sparger was 790 mm/H$_2$O. The pressure loss in the fluidized bed was 2,100 mm/H$_2$O. The results set forth in Table 5 were obtained.

TABLE 5

|  | Unreacted propylene (vol %) |
| --- | --- |
| Central portion | 0.15 |
| Peripheral portion | 0.40 |

In the present invention, the pressure loss in oxygen-containing gas and mixed olefin gas in the fluidized bed reactor in ammoxydation reaction is controlled to provide remarkable improvements in the fluidity of the fluidized bed. Thus, the concentration of unreacted olefin at the peripheral portion of the reaction is lowered. Further, the difference in the concentration of unreacted olefin between the peripheral portion of the reactor and the central portion of the reactor is reduced. Accordingly, the conversion at the peripheral portion of the reactor is remarkably enhanced. Thus, the enhancement of the yield of unsaturated nitrile can be realized.

We claim:

1. A process for producing an $\alpha,\beta$-unsaturated nitrile, said process comprising the step of:

reacting (1) a hydrocarbon selected from an olefin selected from propylene and isobutylene, a paraffin selected from propane and butane, and tertiary butyl alcohol, (2) ammonia, and (3) an oxygen-containing gas, in a reactor at a high temperature in a gas phase over a fluidized bed, so as to prepare an $\alpha,\beta$-unsaturated nitrile having the same number of carbon atoms as said hydrocarbon as a starting material, said reactor comprising a reactor vessel having therein, from a bottom of said reactor vessel, an oxygen-containing gas dispersing plate or pipe and a mixed gas dispersing pipe for dispersing a mixed gas of said hydrocarbon and said ammonia, a pressure loss in said oxygen-containing gas dispersing plate or pipe is controlled to the range of from 0.6 to 3.0 times a pressure loss in said fluidized bed.

2. A process as claimed in claim 1, wherein a pressure loss in said mixed gas dispersing pipe is controlled to the range of from 0.6 to 5.0 times a pressure loss in said fluidized bed.

3. A process as claimed in claim 1, wherein said pressure loss in said oxygen-containing gas dispersing plate or pipe is controlled to the range of from 1.0 to 3.0 times a pressure loss in said fluidized bed.

4. A process as claimed in claim 2, wherein said pressure loss in said mixed gas dispersing pipe is controlled to the range of from 1.0 to 5.0 times a pressure loss in said fluidized bed.

5. A process as claimed in claim 1, wherein said oxygen-containing gas dispersing plate or pipe has a differential pressure adjusting orifice having an opening ratio (opening area of orifice)/(sectional area of reactor) of from 0.10 to 1.0%.

6. A process as claimed in claim 5, wherein said oxygen-containing gas dispersing plate or pipe has a differential pressure adjusting orifice having an opening ratio (opening area of orifice)/(sectional area of reactor) of from 0.12 to 0.35%.

7. A process as claimed in claim 2, wherein said mixed gas dispersing pipe has a differential pressure adjusting orifice having an opening ratio (opening area of orifice)/(sectional area of reactor) of from 0.01 to 0.2%.

8. A process as claimed in claim 7, wherein said mixed gas dispersing pipe has a differential pressure adjusting orifice having an opening ratio (opening area of orifice)/(sectional area of reactor) of from 0.015 to 0.15%.

9. A process as claimed in claim 1 or 2, wherein said pressure loss in said mixed gas dispersing pipe is greater than that of said oxygen-containing gas dispersing plate or pipe.

10. A process as claimed in claim 3 or 4, wherein said pressure loss in said mixed gas dispersing pipe is greater than that of said oxygen-containing gas dispersing plate or pipe.

11. A process as claimed in claim 1 or 3, wherein a feeding temperature of said oxygen-containing gas is controlled to 50° to 500° C., so as to control said pressure loss in said oxygen-containing gas dispersing plate or pipe.

12. A process as claimed in claim 1 or 3, wherein said oxygen-containing gas dispersing plate or pipe has a nozzle comprising an orifice portion for adjusting a differential pressure and a shroud portion for jetting said oxygen-containing gas, and a ratio of a sectional opening area of said orifice portion to that of said shroud portion (sectional opening area of orifice portion/sectional opening area of shroud portion) is from 0.05 to 0.50.

13. A process as claimed in claim 2 or 4, wherein said mixed gas dispersing pipe has a nozzle comprising an orifice portion for adjusting a differential pressure and a shroud portion for jetting said mixed gas, and a ratio of a sectional opening area of said orifice portion to that of said shroud portion (sectional opening area of orifice portion/sectional opening area of shroud portion) is from 0.05 to 0.50.

14. A process as claimed in claim 1 or 2, wherein said hydrocarbon is an olefin selected from propylene and isobutylene.

* * * * *